US012431221B2

(12) United States Patent
Avey et al.

(10) Patent No.: US 12,431,221 B2
(45) Date of Patent: *Sep. 30, 2025

(54) WINDOW-BASED METHOD FOR DETERMINING INHERITED SEGMENTS

(71) Applicant: 23andMe, Inc., Sunnyvale, CA (US)

(72) Inventors: Linda Avey, Lafayette, CA (US); Oleksiy Khomenko, Stanford, CA (US); Brian Thomas Naughton, Mountain View, CA (US); Serge Saxonov, Oakland, CA (US); Anne Wojcicki, Palo Alto, CA (US); Alexander Wong, Palo Alto, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,002

(22) Filed: Dec. 8, 2023

(65) Prior Publication Data

US 2024/0112758 A1    Apr. 4, 2024

Related U.S. Application Data

(63) Continuation of application No. 18/198,699, filed on May 17, 2023, now Pat. No. 11,875,879, which is a
(Continued)

(51) Int. Cl.
    *G06F 16/00*     (2019.01)
    *G16B 20/20*     (2019.01)
    (Continued)

(52) U.S. Cl.
    CPC ............ *G16B 45/00* (2019.02); *G16B 20/20* (2019.02); *G16B 20/40* (2019.02); *G16B 10/00* (2019.02); *G16B 20/00* (2019.02); *G16B 30/00* (2019.02)

(58) Field of Classification Search
    None
    See application file for complete search history.

(56) References Cited

U.S. PATENT DOCUMENTS 5,376,526 A     12/1994   Brown
6,750,011 B1     6/2004   Perlin
(Continued)

FOREIGN PATENT DOCUMENTS

AU     2005289765 A1 *   4/2007   ........... C12Q 1/6816
CA     2632230 A1 *   5/2007   ........... C12Q 1/6806
(Continued)

OTHER PUBLICATIONS

Avalos, et al. "Mendelian Inheritance" Encyclopedia of Molecular Biology (2002) pp. 1-4, John Wiley and Sons Inc. ebook. rretrieved 6/18/20201.
(Continued)

*Primary Examiner* — Tuankhanh D Phan
(74) *Attorney, Agent, or Firm* — McDonnell Boehnen Hulbert & Berghoff LLP

(57) ABSTRACT

Displaying a comparison of genetic data is disclosed, including receiving an indication of a first individual, receiving an indication of a second individual, retrieving the genotypic information for the first individual and the second individual, comparing the genotypic information of the first individual and the second individual, displaying an indication of the comparison of the genotypic information of the first individual and the second individual graphically. A first graphical symbol is used to display an indication of the genome regions for which the first individual and the second individual are identical. A second graphical symbol is used to display an indication of the genome regions for which the first individual and the second individual are half identical.

20 Claims, 8 Drawing Sheets

Related U.S. Application Data continuation of application No. 16/295,399, filed on Mar. 7, 2019, now abandoned, which is a continuation of application No. 12/288,096, filed on Oct. 15, 2008, now Pat. No. 10,275,569.

(60) Provisional application No. 60/999,065, filed on Oct. 15, 2007.

(51) Int. Cl.
*G16B 20/40* (2019.01)
*G16B 45/00* (2019.01)
*G16B 10/00* (2019.01)
*G16B 20/00* (2019.01)
*G16B 30/00* (2019.01)

(56) References Cited

U.S. PATENT DOCUMENTS

| | | |
|---|---|---|
| 6,812,339 B1 | 11/2004 | Venter |
| 7,797,302 B2 | 9/2010 | Kenedy |
| 7,818,281 B2 | 10/2010 | Kennedy |
| 7,818,310 B2 | 10/2010 | Kenedy |
| 7,844,609 B2 | 11/2010 | Kenedy |
| 7,917,438 B2 | 3/2011 | Kenedy |
| 7,933,912 B2 | 4/2011 | Kenedy |
| 7,941,329 B2 | 5/2011 | Kenedy |
| 7,941,434 B2 | 5/2011 | Kenedy |
| 7,957,907 B2 | 6/2011 | Sorenson |
| 8,024,348 B2 | 9/2011 | Kenedy |
| 8,051,033 B2 | 11/2011 | Kenedy |
| 8,055,643 B2 | 11/2011 | Kenedy |
| 8,065,324 B2 | 11/2011 | Kenedy |
| 8,099,424 B2 | 1/2012 | Kenedy |
| 8,108,406 B2 | 1/2012 | Kenedy |
| 8,185,461 B2 | 5/2012 | Kenedy |
| 8,187,811 B2 | 5/2012 | Eriksson |
| 8,200,509 B2 | 6/2012 | Kenedy |
| 8,209,319 B2 | 6/2012 | Kenedy |
| 8,224,835 B2 | 7/2012 | Kenedy |
| 8,255,403 B2 | 8/2012 | Kenedy |
| 8,326,648 B2 | 12/2012 | Kenedy |
| 8,386,519 B2 | 2/2013 | Kenedy |
| 8,428,886 B2 | 4/2013 | Wong |
| 8,452,619 B2 | 5/2013 | Kenedy |
| 8,458,097 B2 | 6/2013 | Kenedy |
| 8,458,121 B2 | 6/2013 | Kenedy |
| 8,463,554 B2 | 6/2013 | Hon |
| 8,510,057 B1 | 8/2013 | Avey |
| 8,543,339 B2 | 9/2013 | Wojcicki |
| 8,589,437 B1 | 11/2013 | Khomenko |
| 8,606,761 B2 | 12/2013 | Kenedy |
| 8,645,343 B2 | 2/2014 | Wong |
| 8,655,899 B2 | 2/2014 | Kenedy |
| 8,655,908 B2 | 2/2014 | Kenedy |
| 8,655,915 B2 | 2/2014 | Kenedy |
| 8,738,297 B2 | 5/2014 | Sorenson |
| 8,786,603 B2 | 7/2014 | Rasmussen |
| 8,788,283 B2 | 7/2014 | Kenedy |
| 8,788,286 B2 | 7/2014 | Kenedy |
| 8,855,935 B2 | 10/2014 | Myres |
| 8,990,250 B1 | 3/2015 | Chowdry |
| 9,031,870 B2 | 5/2015 | Kenedy |
| 9,116,882 B1 | 8/2015 | Macpherson |
| 9,170,992 B2 | 10/2015 | Kenedy |
| 9,213,944 B1 | 12/2015 | Do |
| 9,213,947 B1 | 12/2015 | Do |
| 9,218,451 B2 | 12/2015 | Wong |
| 9,336,177 B2 | 5/2016 | Hawthorne |
| 9,367,663 B2 | 6/2016 | Deciu |
| 9,367,800 B1 | 6/2016 | Do |
| 9,390,225 B2 | 7/2016 | Barber |
| 9,405,818 B2 | 8/2016 | Chowdry |
| 9,582,647 B2 | 2/2017 | Kenedy |
| 9,836,576 B1 | 12/2017 | Do |
| 9,864,835 B2 | 1/2018 | Avey |
| 9,977,708 B1 | 5/2018 | Do |
| 10,025,877 B2 | 7/2018 | Macpherson |
| 10,162,880 B1 | 12/2018 | Chowdry |
| 10,275,569 B2 | 4/2019 | Avey |
| 10,296,847 B1 | 5/2019 | Do |
| 10,379,812 B2 | 8/2019 | Kenedy |
| 10,432,640 B1 | 10/2019 | Hawthorne |
| 10,437,858 B2 | 10/2019 | Naughton |
| 10,516,670 B2 | 12/2019 | Hawthorne |
| 10,572,831 B1 | 2/2020 | Do |
| 10,643,740 B2 | 5/2020 | Avey |
| 10,658,071 B2 | 5/2020 | Do |
| 10,691,725 B2 | 6/2020 | Naughton |
| 10,699,803 B1 | 6/2020 | Do |
| 10,755,805 B1 | 8/2020 | Do |
| 10,777,302 B2 | 9/2020 | Chowdry |
| 10,790,041 B2 | 9/2020 | Macpherson |
| 10,803,134 B2 | 10/2020 | Kenedy |
| 10,841,312 B2 | 11/2020 | Hawthorne |
| 10,854,318 B2 | 12/2020 | Macpherson |
| 10,891,317 B1 | 1/2021 | Chowdry |
| 10,896,233 B2 | 1/2021 | Kenedy |
| 10,936,626 B1 | 3/2021 | Naughton |
| 10,957,455 B2 | 3/2021 | Kenedy |
| 10,991,467 B2 | 4/2021 | Kenedy |
| 10,999,285 B2 | 5/2021 | Hawthorne |
| 11,003,694 B2 | 5/2021 | Kenedy |
| 11,031,101 B2 | 6/2021 | Hon |
| 11,049,589 B2 | 6/2021 | Hon |
| 11,170,047 B2 | 11/2021 | Macpherson |
| 11,170,873 B2 | 11/2021 | Avey |
| 11,171,962 B2 | 11/2021 | Hawthorne |
| 11,875,879 B1 * | 1/2024 | Avey ............... G16B 20/20 |
| 2003/0172065 A1 * | 9/2003 | Sorenson ............ G16B 10/00 |
| 2004/0081996 A1 * | 4/2004 | Landers ............. G16B 20/20 |
| | | 435/6.11 |
| 2004/0126840 A1 | 7/2004 | Cheng |
| 2004/0229231 A1 | 11/2004 | Frudakis |
| 2004/0241730 A1 | 12/2004 | Yakhini |
| 2004/0248086 A9 | 12/2004 | Ginns |
| 2005/0089852 A1 | 4/2005 | Lee |
| 2005/0147947 A1 | 7/2005 | Cookson, Jr. |
| 2007/0037182 A1 | 2/2007 | Gaskin |
| 2007/0250809 A1 | 10/2007 | Kennedy |
| 2008/0131887 A1 | 6/2008 | Stephan |
| 2008/0227063 A1 | 9/2008 | Kenedy |
| 2008/0228043 A1 | 9/2008 | Kenedy |
| 2008/0228410 A1 | 9/2008 | Kenedy |
| 2008/0228451 A1 | 9/2008 | Kenedy |
| 2008/0228677 A1 | 9/2008 | Kenedy |
| 2008/0228698 A1 | 9/2008 | Kenedy |
| 2008/0228699 A1 | 9/2008 | Kenedy |
| 2008/0228700 A1 | 9/2008 | Kenedy |
| 2008/0228701 A1 | 9/2008 | Kenedy |
| 2008/0228702 A1 | 9/2008 | Kenedy |
| 2008/0228704 A1 | 9/2008 | Kenedy |
| 2008/0228705 A1 | 9/2008 | Kenedy |
| 2008/0228706 A1 | 9/2008 | Kenedy |
| 2008/0228708 A1 | 9/2008 | Kenedy |
| 2008/0228722 A1 | 9/2008 | Kenedy |
| 2008/0228753 A1 | 9/2008 | Kenedy |
| 2008/0228756 A1 | 9/2008 | Kenedy |
| 2008/0228757 A1 | 9/2008 | Kenedy |
| 2008/0228765 A1 | 9/2008 | Kenedy |
| 2008/0228766 A1 | 9/2008 | Kenedy |
| 2008/0228767 A1 | 9/2008 | Kenedy |
| 2008/0228768 A1 | 9/2008 | Kenedy |
| 2008/0228797 A1 | 9/2008 | Kenedy |
| 2008/0243843 A1 | 10/2008 | Kenedy |
| 2009/0043752 A1 | 2/2009 | Kenedy |
| 2009/0099789 A1 | 4/2009 | Stephan |
| 2009/0112871 A1 | 4/2009 | Hawthorne |
| 2009/0118131 A1 | 5/2009 | Avey |
| 2009/0119083 A1 | 5/2009 | Avey |
| 2010/0042438 A1 | 2/2010 | Moore |
| 2010/0063830 A1 | 3/2010 | Kenedy |
| 2010/0063835 A1 | 3/2010 | Kenedy |
| 2010/0063865 A1 | 3/2010 | Kenedy |

(56) References Cited

U.S. PATENT DOCUMENTS

| | | |
|---|---|---|
| 2010/0063930 A1 | 3/2010 | Kenedy |
| 2010/0070292 A1 | 3/2010 | Kenedy |
| 2010/0070455 A1 | 3/2010 | Halperin |
| 2010/0076950 A1 | 3/2010 | Kenedy |
| 2010/0076988 A1 | 3/2010 | Kenedy |
| 2010/0169262 A1 | 7/2010 | Kenedy |
| 2010/0169313 A1 | 7/2010 | Kenedy |
| 2010/0169338 A1 | 7/2010 | Kenedy |
| 2010/0223281 A1 | 9/2010 | Hon |
| 2011/0078168 A1 | 3/2011 | Kenedy |
| 2011/0184656 A1 | 7/2011 | Kenedy |
| 2012/0270190 A1 | 10/2012 | Kenedy |
| 2012/0270794 A1 | 10/2012 | Eriksson |
| 2013/0345988 A1 | 12/2013 | Avey |
| 2014/0006433 A1 | 1/2014 | Hon |
| 2014/0067355 A1 | 3/2014 | Noto |
| 2015/0227610 A1 | 8/2015 | Chowdry |
| 2015/0248473 A1 | 9/2015 | Kenedy |
| 2015/0347566 A1 | 12/2015 | Kenedy |
| 2016/0026755 A1 | 1/2016 | Byrnes |
| 2016/0042143 A1 | 2/2016 | Kenedy |
| 2016/0103950 A1 | 4/2016 | Myres |
| 2016/0171155 A1 | 6/2016 | Do |
| 2016/0277408 A1 | 9/2016 | Hawthorne |
| 2016/0350479 A1 | 12/2016 | Han |
| 2017/0011042 A1 | 1/2017 | Kermany |
| 2017/0017752 A1 | 1/2017 | Noto |
| 2017/0053089 A1 | 2/2017 | Kenedy |
| 2017/0185719 A1 | 6/2017 | Kenedy |
| 2017/0220738 A1 | 8/2017 | Barber |
| 2017/0228498 A1 | 8/2017 | Hon |
| 2017/0277827 A1 | 9/2017 | Granka |
| 2017/0277828 A1 | 9/2017 | Avey |
| 2017/0329866 A1 | 11/2017 | Macpherson |
| 2017/0329891 A1 | 11/2017 | Macpherson |
| 2017/0329899 A1 | 11/2017 | Bryc |
| 2017/0329901 A1 | 11/2017 | Chowdry |
| 2017/0329902 A1 | 11/2017 | Bryc |
| 2017/0329904 A1 | 11/2017 | Naughton |
| 2017/0329915 A1 | 11/2017 | Kittredge |
| 2017/0329924 A1 | 11/2017 | Macpherson |
| 2017/0330358 A1 | 11/2017 | Macpherson |
| 2018/0181710 A1 | 6/2018 | Avey |
| 2018/0210705 A1 | 7/2018 | Kenedy |
| 2018/0307778 A1 | 10/2018 | Macpherson |
| 2019/0012431 A1 | 1/2019 | Hon |
| 2019/0034163 A1 | 1/2019 | Kenedy |
| 2019/0267115 A1 | 8/2019 | Avey |
| 2019/0281061 A1 | 9/2019 | Hawthorne |
| 2019/0384777 A1 | 12/2019 | Naughton |
| 2020/0137063 A1 | 4/2020 | Hawthorne |
| 2020/0210143 A1 | 7/2020 | Kenedy |
| 2020/0372974 A1 | 11/2020 | Chowdry |
| 2021/0020266 A1 | 1/2021 | Freyman |
| 2021/0043278 A1 | 2/2021 | Hon |
| 2021/0043279 A1 | 2/2021 | Hon |
| 2021/0043280 A1 | 2/2021 | Hon |
| 2021/0043281 A1 | 2/2021 | Macpherson |
| 2021/0058398 A1 | 2/2021 | Hawthorne |
| 2021/0082167 A1 | 3/2021 | Jewett |
| 2021/0166452 A1 | 6/2021 | Jewett |
| 2021/0166823 A1 | 6/2021 | Kenedy |
| 2021/0193257 A1 | 6/2021 | Freyman |
| 2021/0209134 A1 | 7/2021 | Kenedy |
| 2021/0225458 A1 | 7/2021 | Hon |
| 2021/0233665 A1 | 7/2021 | Kenedy |
| 2021/0243094 A1 | 8/2021 | Holness |
| 2021/0250357 A1 | 8/2021 | Hawthorne |
| 2021/0313013 A1 | 10/2021 | Hon |
| 2021/0375392 A1 | 12/2021 | Polcari |

FOREIGN PATENT DOCUMENTS

| | | | |
|---|---|---|---|
| WO | 20060116622 | W | 11/2006 |
| WO | 2007084902 | A2 | 7/2007 |
| WO | 2009051768 | A1 | 4/2009 |
| WO | 2016073953 | W | 5/2016 |

OTHER PUBLICATIONS

Caballero V, Preliminary molecular genetic analysis of the Receptor Interacting Protein 140 (RIP140) in women affected by endometriosis. J Exp Clin Assist Reprod. Aug. 30, 2005;2:11. doi: 10.1186/1743-1050-2-11. PMID: 16131398; PMCID: PMC1242355.

Horton R, et al., Gene map of the extended human MHC. Nat Rev Genet. Dec. 2004;5(12):889-99. doi: 10.1038/nrg1489. PMID: 15573121.

Human Genome Landmarks Poster, United States Department of Energy (DOE), p. 6. [retrieved on Jan. 27, 2007] <URL:http//web.archive.org/web/20070127170426/http://www.ornl.gov/sci/techresources/Human Genome/posters/ chromosome/ chooser. shtml>.

International Search Report and Written Opinion, PCT Application PCT/US2008/011806, mailed Dec. 10, 2008.

International Search Report and Written Opinion, PCT Application PCT/US2008/011833, mailed Dec. 29, 2008.

Lightfoot et al. Quantitative trait loci associated with maximal exercise endurance in mice. (2007) J Applied Physiol. vol. 103, p. 105-110. (Year: 2007).

Nievergelt CM, Suggestive evidence for association of the circadian genes PERIOD3 and ARNTL with bipolar disorder. Am J Med Genet B Neuropsychiatr Genet. Apr. 5, 2006;141B(3):234-41. doi: 10.1002/ajmg.b.30252. PMID: 16528748; PMCID: PMC2651679.

Notice of Allowance, U.S. Appl. No. 12/288,026, mailed Sep. 12, 2017.

Notice of Allowance, U.S. Appl. No. 12/288,096, mailed Nov. 26, 2018.

Notice of Allowance, U.S. Appl. No. 15/829,782, mailed Jun. 18, 2021.

Notice of Allowance, U.S. Appl. No. 16/409,574, mailed Jan. 3, 2020.

Notice of Allowance, U.S. Appl. No. 18/198,699, mailed Sep. 28, 2023.

Office Action, U.S. Appl. No. 12/288,026, mailed Jul. 21, 2011.
Office Action, U.S. Appl. No. 12/288,026, mailed Dec. 19, 2011.
Office Action, U.S. Appl. No. 12/288,026, mailed Oct. 2, 2013.
Office Action, U.S. Appl. No. 12/288,026, mailed Apr. 16, 2014.
Office Action, U.S. Appl. No. 12/288,026, mailed Dec. 4, 2014.
Office Action, U.S. Appl. No. 12/288,026, mailed May 22, 2015.
Office Action, U.S. Appl. No. 12/288,026, mailed Sep. 9, 2016.
Office Action, U.S. Appl. No. 12/288,026, mailed Apr. 27, 2017.
Office Action, U.S. Appl. No. 12/288,096, mailed Jul. 21, 2011.
Office Action, U.S. Appl. No. 12/288,096, mailed Dec. 19, 2011.
Office Action, U.S. Appl. No. 12/288,096, mailed Jun. 13, 2013.
Office Action, U.S. Appl. No. 12/288,096, mailed Dec. 19, 2013.
Office Action, U.S. Appl. No. 12/288,096, mailed Aug. 6, 2014.
Office Action, U.S. Appl. No. 12/288,096, mailed Mar. 19, 2015.
Office Action, U.S. Appl. No. 12/288,096, mailed Jul. 22, 2015.
Office Action, U.S. Appl. No. 12/288,096, mailed Jan. 11, 2016.
Office Action, U.S. Appl. No. 12/288,096, mailed Sep. 9, 2016.
Office Action, U.S. Appl. No. 12/288,096, mailed Apr. 28, 2017.
Office Action, U.S. Appl. No. 12/288,096, mailed Mar. 13, 2018.
Office Action, U.S. Appl. No. 15/829,782, mailed Jun. 23, 2020.
Office Action, U.S. Appl. No. 15/829,782, mailed Mar. 1, 2021.
Office Action, U.S. Appl. No. 16/295,399, mailed Oct. 18, 2022.
Office Action, U.S. Appl. No. 16/295,399, mailed Apr. 5, 2023.
Office Action, U.S. Appl. No. 16/409,574, mailed Sep. 17, 2019.
Office Action, U.S. Appl. No. 18/198,699, mailed Aug. 15, 2023.

Osier, et al., "ALFRED: An allele frequency database for anthropology," American Journal of Physical Anthropology, vol. 119, No. 1, Aug. 14, 2002, pp. 77-83. <doi: 10 . 1002/aipa. 1 0094>.

Pearson, W.R., et al. "Improved tools for biological sequence comparison," Proceedings of the National Academy of Sciences (PNAS), Biochemistry, vol. 85, No. 8, Apr. 1, 1988, pp. 2444-2448.

(56) References Cited

OTHER PUBLICATIONS

Poznik, et al., "A novel framework for sib pair linkage analysis," The American Journal Human Genetics, vol. 78, Feb. 2006, pp. 222-230.
Purcell, et al., "PLINK: a toolset for whole-genome association and population-based linkage analysis", Am. J. Hum. Genet., vol. 81, Sep. 2007, pp. 559-575.
Rao, et al., "SAGE Programs; Model free linkage analysis for complex cardiovascular phentyopes," Methods in Molecular Medicine, vol. 128, chapter 6, (2006) pp. 61-89.
Reed DR, Diverse tastes: Genetics of sweet and bitter perception. Physiol Behav. Jun. 30, 2006;88(3):215-26. doi: 10.1016/j.physbeh. 2006.05.033. Epub Jun. 19, 2006. PMID: 16782140; PMCID: PMC1698869.
Scuteri A, Genome-wide association scan shows genetic variants in the FTO gene are associated with obesity-related traits. PLoS Genet. Jul. 2007;3(7):e115. doi: 10.1371/journal.pgen. 0030115. PMID: 17658951; PMCID: PMC1934391.
Yang, et al., "Linkers: A simulation programming system for generating populations with genetic structure" Computers in Biology and Medicine, vol. 20, No. 2, 1990, pp. 135-144.

* cited by examiner

FIG. 3b family inheritance

See what DNA you share with relatives, both close and distant.

me
My Health and Traits (89)
Browse Raw Data
My Profile family & friends
Compare Genes
▶ Family Inheritance my ancestors
Maternal Line
Paternal Line
Ancestry Painting
Global Similarity

23andWe
Introduction
My Surveys
Featured Research account
Genome Sharing
Inbox
Settings
Help/Contact Us

| Genome View | GrandTree |

Tell me how to use this feature...

Compare the genome of: —301c
[Erin Mendel (Daughter) ▼]

To the genome of: —302c
[Ian Mendel (Son) ▼]

Bitter Tasting
Genes related to bitter tasting

—305c

Estimates —304
- Half-identical (1.2 Gb)
- Completely identical (0.73 Gb)
- No Identical
- Not enough SNPs
- ▽ Genes/regions associated with the selected trait.

—303c
Click on a trait below for comparison:

- Genome-Wide Comparison
  Comparison across all of the genome data
- Bitter Tasting
  Genes related to bitter tasting
- Circadian Rhythm
  Genes related to regulating your internal clock
- Endurance
  Genes related to physical endurance
- Female Fertility
  Genes related to fertility in women
- Immune System Compatibility
  Genes related to histocompatibility
- Non-Bitter Tasting
  Genes related to sweet, umami, sour, and spicy tasting
- Pigmentation
  Genes related to skin, eye and hair color
- Weight/Body mass index
  Genes related to weight/body mass index Any set of genes.
[Enter a list of genes separated by comma] Submit Tell Me About...
...using the Genome View.
...how you calculate identity.
...overall similarity between individuals.
...whether I am related to my spouse.

FIG. 3c

WINDOW-BASED METHOD FOR DETERMINING INHERITED SEGMENTS

CROSS-REFERENCE TO RELATED APPLICATIONS

This application is a continuation of and claims priority to U.S. patent application Ser. No. 18/198,699, filed May 17, 2023, which is hereby incorporated by reference in its entirety.

U.S. patent application Ser. No. 18/198,699 is a continuation of and claims priority to U.S. patent application Ser. No. 16/295,399, filed Mar. 7, 2019, which is hereby incorporated by reference in its entirety.

U.S. patent application Ser. No. 16/295,399 is a continuation of and claims priority to U.S. patent application Ser. No. 12/288,096, filed Oct. 15, 2008, which is hereby incorporated by reference in its entirety.

U.S. patent application Ser. No. 12/288,096 claims priority to U.S. provisional patent application No. 60/999,065, filed Oct. 15, 2007, which is hereby incorporated by reference in its entirety.

BACKGROUND OF THE INVENTION

The instructions for making the cells in the human body are encoded in deoxyribonucleic acid (DNA). DNA is a long, ladder-shaped molecule, in which each corresponding rung is made up of a pair of interlocking units, called bases, that are designated by the four letters in the DNA alphabet—A, T, G and C. 'A' always pairs with 'T', and 'G' always pairs with 'C'. The sequence of these four letters that make up an individual's DNA is referred to as the individual's genome.

The long molecules of DNA in cells are organized into pieces called chromosomes. Humans have 23 pairs of chromosomes. Other organisms have different numbers of pairs—for example, chimpanzees have 24 pairs. Chromosomes are further organized into short segments of DNA called genes. The different letters A, T, G, and C, which make up a gene, dictate how cells function and what traits to express by dictating what proteins the cells will make Proteins do much of the work in the body's cells. Some proteins give cells their shape and structure. Others help cells carry out biological processes like digesting food or carrying oxygen in the blood. Using different combinations of the As, Cs, Ts and Gs, DNA creates the different proteins and regulates when and how they are turned on. Information about an individual's DNA sequence, including his or her genome or particular regions of the genome is referred to as genotypic information. Regions of a particular individual's genome can also be referred to as "DNA sequences."

Each person has the same set of genes—about 20,000 in all. The differences between people come from slight variations in these genes. For example, it's not that a person with red hair has the "red hair gene" while a person with brown hair has the "brown hair gene." Rather, all people have genes for hair color, and different versions of these genes, i.e. differences in the regions of the genome containing the gene, dictate whether someone will be a redhead or a brunette.

Variations in DNA sequences can generate biological variations between people by causing differences in the recipes for proteins that are written in genes. Those differences can in turn influence a variety of traits such as appearance, disease susceptibility or response to drugs. While some differences in the DNA sequences among individuals lead to differences in health or physical appearance, some variations in the DNA sequences among individuals seem to lead to no observable differences between people at all.

Every region of a person's autosomal (restricted to "non-sex" chromosomes) genome is represented by a pair of DNA sequences, one inherited from the mother and one from the father. Also, each child inherits virtually 50% of his or her DNA from the father and virtually 50% from the mother. The DNA inherited from the mother can be either inherited from the maternal grandmother or the maternal grandfather. The DNA inherited from the father can be inherited from the paternal grandfather or the paternal grandmother. Because each parent has two DNA sequences for every genomic region only one of which he or she will pass to each child, two siblings may inherit the same sequence from the father or the same sequence from the mother, the same sequence from both, or different sequences from each parent. As relationships become more distant, there is a lower likelihood that two individuals will have the same sequence. Because it is useful to know the similarity between two individuals' DNA, it would be useful to have a method for comparing the genotypic information of at least two individuals and displaying the comparison in a way that can be easy to understand.

BRIEF DESCRIPTION OF THE DRAWINGS

Various embodiments of the invention are disclosed in the following detailed description and the accompanying drawings.

FIG. 3b is a screen shot illustrating another example of an interface displaying an indication of the similarity between two individual's genotypic information.

FIG. 3c is a screenshot illustrating another example of an interface displaying an indication of the similarity between two individuals' genotypic information.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
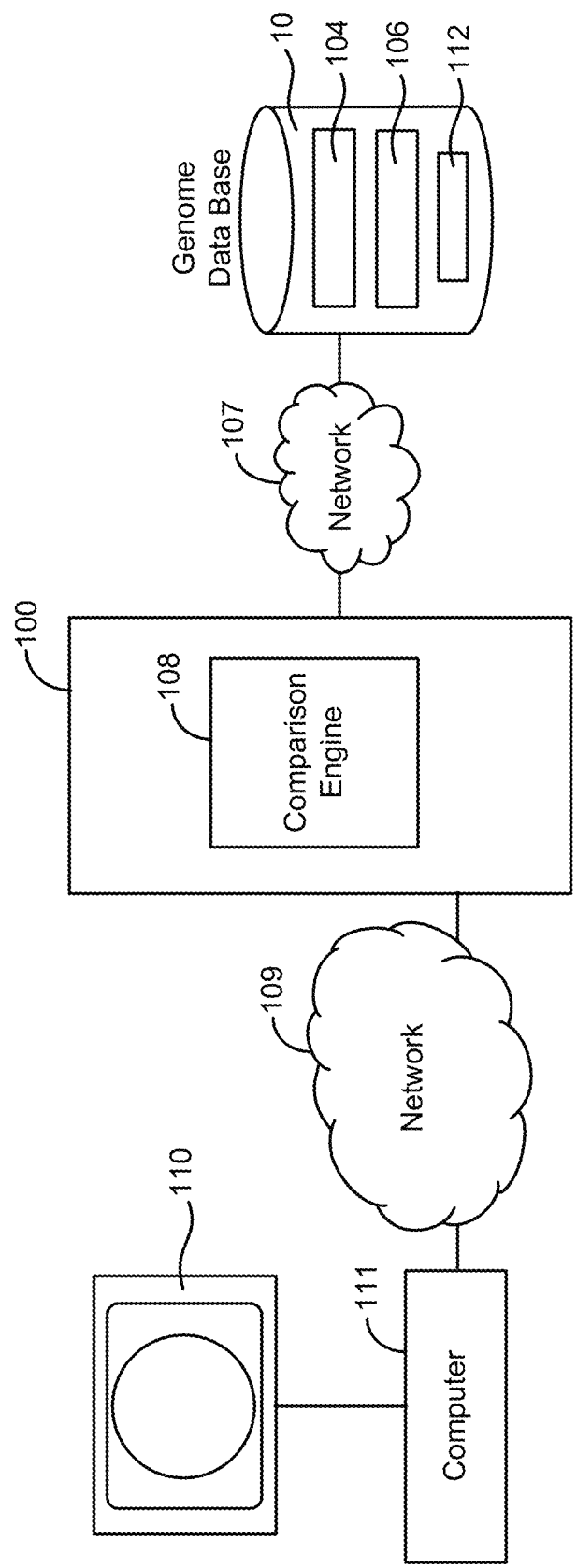
FIG. 1 is a block diagram illustrating an embodiment of a system for displaying similarities in the genotypic data between at least two individuals.

FIG. 1 is a block diagram illustrating an embodiment of a system for displaying similarities in the genotypic data between at least two individuals.

In the example shown, system 100 receives an indication of at least two individuals, and then retrieves the genotype information for those individuals. The system 100 may also receive an indication of the relationship between the two individuals, but need not do so. The system 100 may retrieve the genotypic information for the individuals from a variety of sources. For example, as shown in FIG. 1, the system 100 may be connected, for example by a network 107, to a genome database 102, and retrieve the individual's genotypic information from the database 102, which includes the genotypic information for the first individual 104 and the genotypic information for the second individual 106. Alternatively, the genotypic information may be stored in the system 100 or may be received from another source.

The system 100 includes a comparison engine 108 that receives the genotypic information for the at least two individuals 104 and 106 and compares the genotypic information of the at least two individuals. The system may also receive an indication that the comparison should be determined across all of the genome data of the individuals or for the genome data for a particular trait. The system 100 is connected, for example through a network 109 to a computer 111 which is connected to a display 110, for displaying a representation of the similarity between or among the at least two individuals. The display 110 can include any device that will allow for displaying the comparison of the at least two individuals' genotypic information.

Figure 2A:
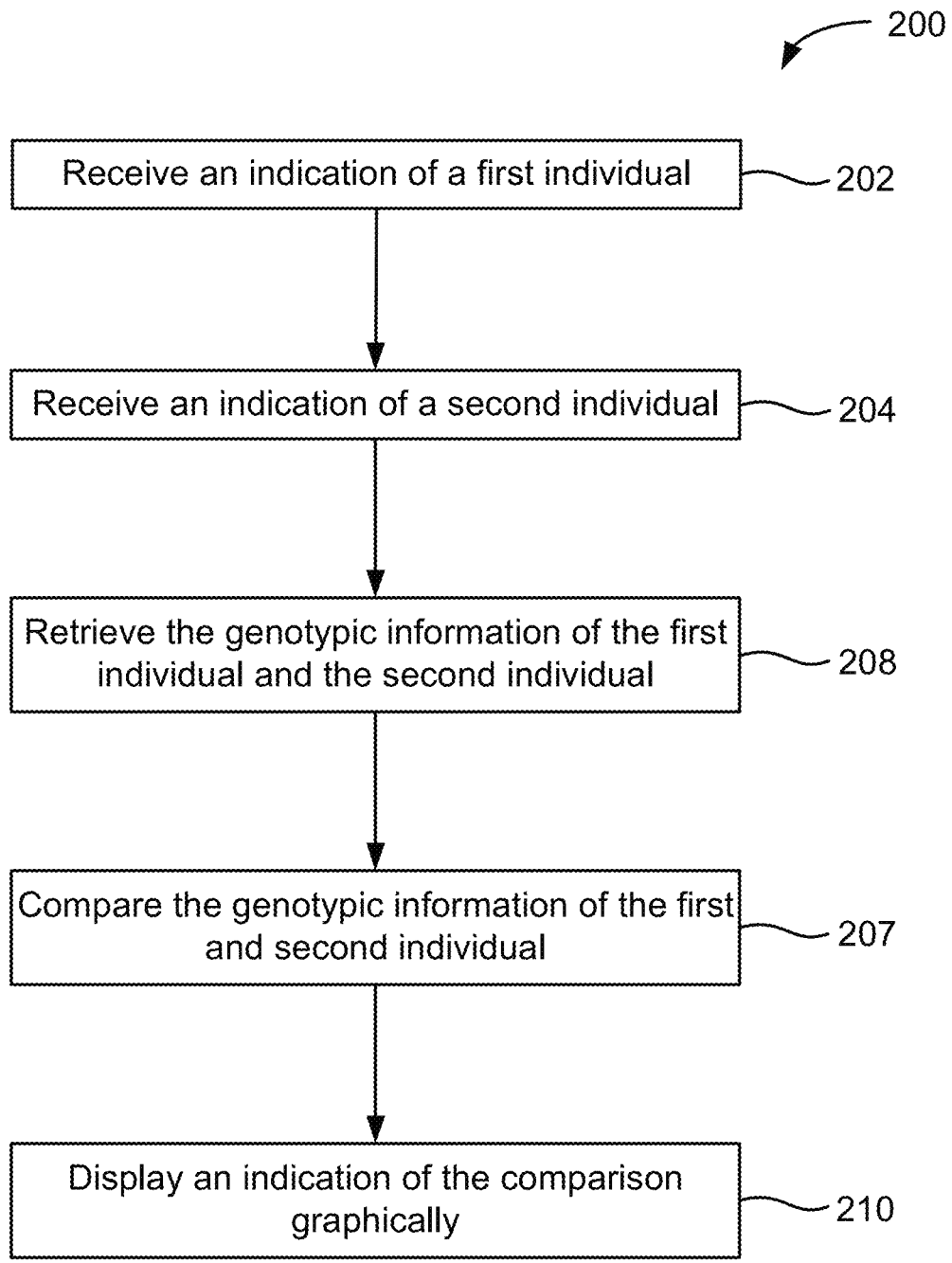
FIG. 2a is a flow chart illustrating an embodiment of a method for displaying similarities in the genotypic data between at least two individuals.
Figure 3A:
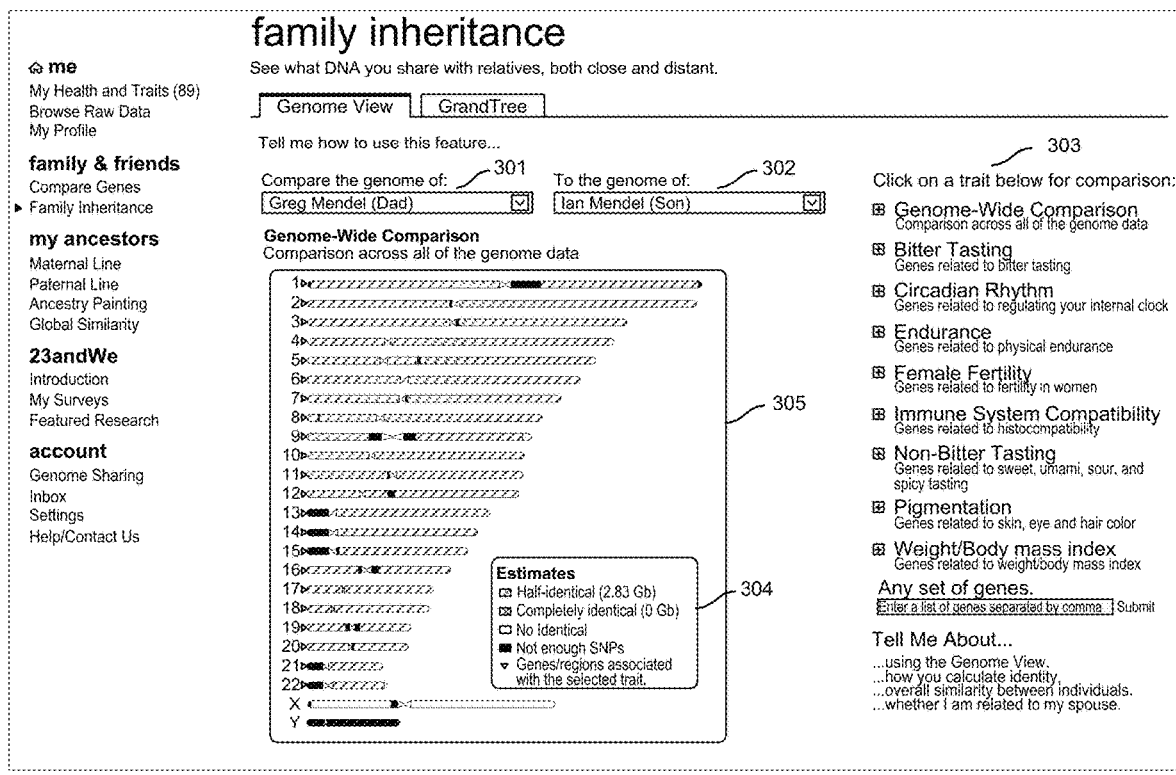
FIG. 3a is a screen shot of an example of an interface for displaying an indication of the comparison of at least two individual's genome data.

FIG. 2a is a flow chart illustrating an embodiment of a method 200 for displaying similarities in the genotypic data between at least two individuals. At 202, an indication of a first individual is received. FIG. 3a is a screen shot of an example of an interface for displaying an indication of the comparison of at least two individual's genome data. In the example shown in FIG. 3a, the interface allows for receiving an indication of a first individual by a user indicating an individual at 301. There are many ways a user may indicate an individual. For example, this indication could be done from a drop down menu, by the user dragging and dropping a name from a list on the screen, or by the user entering the information by typing. This indication could be done by other ways as well. In the example shown in FIG. 3a, "Greg Mendel" is indicated as a first individual. The indication may include the person's position in the family, but need not do so.

Returning to FIG. 2a, at 204, an indication of a second individual is received. In the example shown in FIG. 3a, the interface allows for receiving an indication of a second individual by a user indicating an individual at 302. Again, there are many ways a user may indicate an individual. For example, this indication could be done from a drop down menu, by the user dragging and dropping a name from a list on the screen, or by the user entering the information by typing. This indication could be done by other ways as well. In the example shown in FIG. 3a, "Ian Mendel" is indicated as a first individual. Again, the indication may include the person's position in the family, but need not do so.

At 208, the genotypic information for the first and second individual is retrieved. An example of retrieving the genotypic information is further illustrated in FIG. 1, in which the genotypic information for the first individual 104 and the second individual 106 is retrieved from a genome database coupled to the system 100. As discussed above, this is only an example of retrieving genotypic information for individuals. Genotypic information for an individual can be retrieved from other types of sources.

At 209, the genotypic information of the first individual 104 and second individual 106 is compared. In comparing genotypic information for two individuals, one can expect that more than 99% of the underlying DNA sequence will be the same. However, the less than 1% of the DNA that may differ represents a large number of base pairs. There may be many base pairs that differ in the DNA of two unrelated people from different ethnic groups. On the other hand, when DNA is passed from parent to child it is copied almost exactly. All locations on an individual's genome are represented by two DNA sequences one inherited from the father and one inherited from the mother. Two individuals are half-identical for a DNA region if one of their two sequences is the same at that region. Two individuals are identical for a DNA region if both of their two sequences are the same at that region. Because children inherit virtually 50% of their genomes from each parent, they are half-identical across the genome to each parent. Because a parent's chromosome pairs recombine before being passed on to children, a child receives a mixture of his or her grandparents' genomes. For example, because the DNA a mother passes to her daughter is a mixture of DNA from the maternal grandmother and the maternal grandfather, only patches of a grandchild's genome will be half-identical to each grandparent's genome. Also, because a parent's DNA recombines before being passed to a child, the child's siblings may or may not inherit the same patches of the mother's or father's genome. Because each parent has two DNA sequences at every region of their genomes, only one of which he or she will pass to each child, two siblings may inherit the same sequence from the father for a particular region or the same sequence from the mother for a particular region, the same sequence from both the mother and father, or different sequences from each parent. When two siblings inherit the same sequence of DNA from one parent for a region of the genome, they are half-identical for that region. If they also inherit the same sequence of DNA from the other parent for that region of the genome, they are identical at that region. Identical twin siblings are identical across their entire genome. As relationships become more distant, there is a lower likelihood that two individuals will have the same DNA sequence for a particular region.

Because of recombination of DNA sequences and the independent assortment of chromosomes, the DNA of two parents is shuffled at every generation. That, in addition to the small trickle of new mutations, means that only relatives will carry long genome regions where their DNA is completely or almost completely identical. In order to determine whether a region is identical, one could assay every single base pair directly or assay a large number of markers that vary between individuals. Markers are points along the genome where individuals may differ. These markers could be, but are not limited to, SNPs (Single Nucleotide Polymorphisms), which are points along the genome with two or more common variations. A long stretch of sequence where every marker is the same between two people indicates that the rest of the sequence, which is not being assayed directly, is also identical. If two markers are the same, they are called "Identical By State". If, in addition to being the same, they lie within a region of identical sequence, which is shared because of recent common ancestry, they are "Identical By Descent" or IBD.

Available genotypic information may come in "phased" or "unphased" forms. As explained above, humans have 23 pairs of chromosomes. Every region of a person's autosomal (restricted to "non-sex" chromosomes) genome is represented by a pair of DNA sequences, one inherited from the mother and one from the father. If the genotypic data is "unphased" then it does not specify which of the marker values came from which of the two DNA sequences. With "phased" genotypic data, each of the markers values is specifically associated with one of the two DNA sequences for the chromosomes. The data can also come in a partially phased form where some of the markers have phased information while others do not. At 209, the comparison can be done using any combination of phased, partially-phased or unphased data. An example of a way to find DNA regions that are IBD between two people using unphased SNP genotype data is to scan the genome in windows of 10 Centimorgans ("CM"). For every window the method can compare all the SNP values or genotypes between the two people. If every SNP has the same exact values, then the two people are completely identical along the 10 CM window. If they are not all the same, but every SNP has at least one value (allele) in common between two people, then the two people are half-identical along the window. This method can also allow for a small percentage of errors so that not every SNP has to have the same values or some values in common, to make the determination of identity or half-identity, respectively. Other embodiments may include other methods for determining IBD regions.

Figure 4:
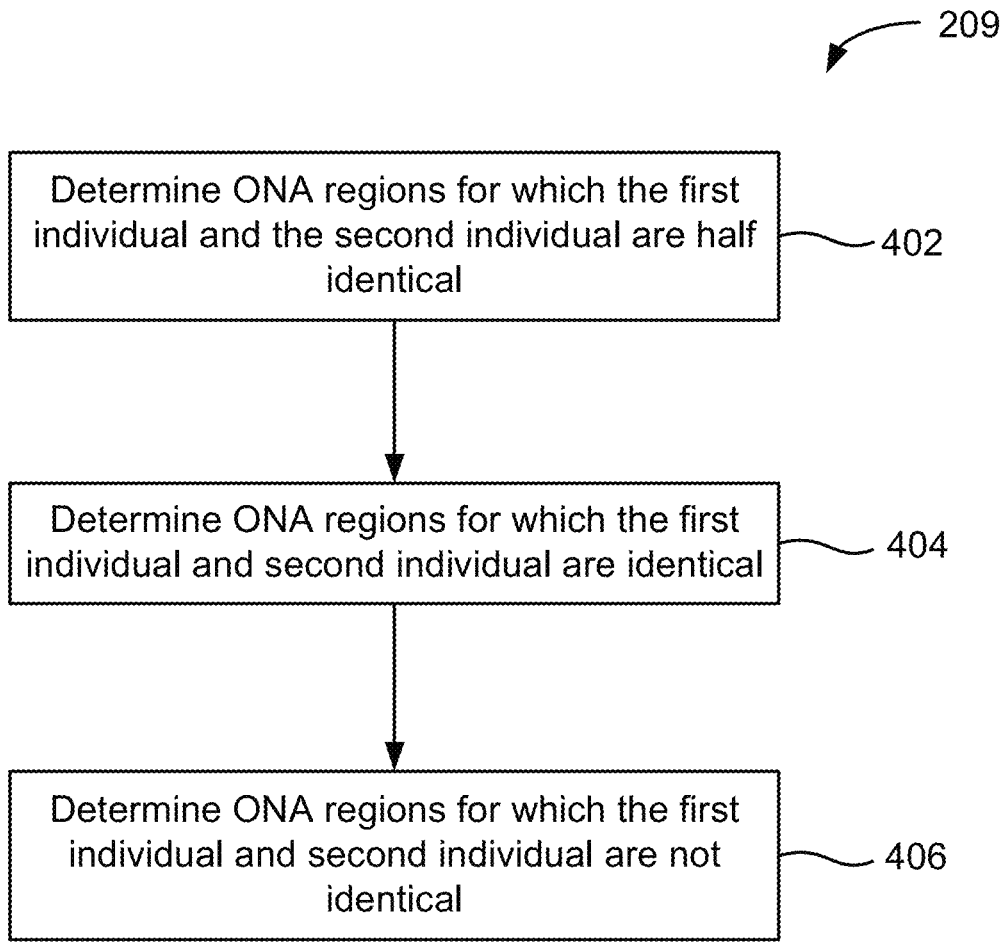
FIG. 4 is a flowchart further illustrating, comparing the genotypic information of at least two individuals.

FIG. 4 is a flowchart further illustrating step 209, comparing the genotypic information of at least two individuals. When the two individuals' DNA is compared, it is determined at 402 for which DNA regions the two individuals have the same DNA sequences. It is also determined at 404, for which regions the individuals are half-identical, i.e. for which regions the two individuals have one sequence in common. It is further determined at 406 for which regions the two individuals are not at all identical, i.e. the regions in which the individuals have none of the same sequences.

Returning to FIG. 2*a*, at step 210, an indication of the similarity between the first and second individual's genotypic information is displayed graphically. FIG. 3*a* is an example illustrating displaying an indication of the similarity between two individuals' genotypic information. In the example in FIG. 3*a*, an indication was received at 301 that a first individual was "Greg Mendel" and an indication was received at 302 that a second individual was "Ian Mendel." In the example in FIG. 3*a*, there is an indication at 301 that "Greg Mendel" is the father and an indication at 302 that "Ian Mendel" is the son. However, an indication of the relationship between two individuals need not be received.

FIG. 3*a* is a screen shot illustrating an example of an interface displaying an indication of the similarity between two individuals' genotypic information. As illustrated in the example in FIG. 3*a* at 305, an indication of each of the 22 pairs of autosomal human chromosomes and the X and Y chromosomes is displayed. As shown at 305 and 304, different colored graphical symbols are used to indicate the similarity between the genotypic information of at least two individuals. As used herein, a graphical symbol can include a graphical object displayed on a screen of any appropriate size, shape, and color. In the example shown in FIG. 3*a* at 304, a blue symbol (in this case, a rectangle, or a semicircle if it is on the edge of the chromosome, as shown in FIG. 3*a*) is used to display an indication of which locations on the chromosome pairs two individuals are half-identical. In other words, the locations at which one of the two DNA sequences making up the individuals' genomes is the same are indicated. A black symbol is used to display an indication of which locations on the chromosome pairs two individual are identical. In other words, the locations at which both of the two DNA sequences making up the two individuals' genomes is the same are indicated. A white symbol is used to indicate which locations are not identical and a grey symbol is used to indicate for which locations there are not enough genotypic data to make a determination. However, in alternate embodiments other symbols or colors could be used to display indications of these same type of similarities in genotypic information.

In the example in FIG. 3*a*, an indication is displayed that Greg Mendel is half identical to Ian Mendel at all autosomal chromosome pairs, except for those locations in which there is not enough genotypic data. In particular, the indication for all of the chromosome pairs, except those with not enough data are colored blue. Because Greg Mendel is Ian Mendel's father, we know that Ian Mendel inherited virtually 50% of his DNA from Greg Mendel, and thus would be half-identical at virtually all locations on the chromosome pairs.

Figure 3B:
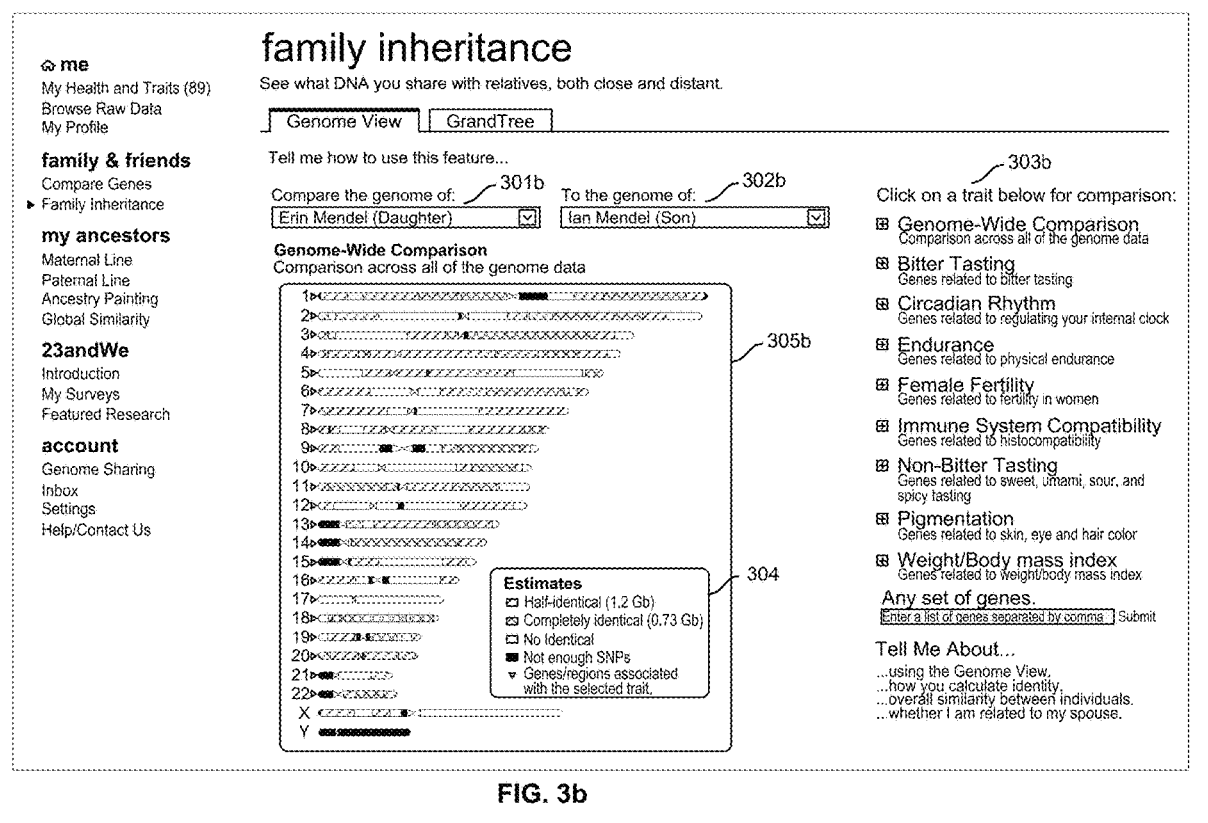

FIG. 3*b* is a screen shot illustrating another example of an interface displaying an indication of the similarity between two individual's genotypic information. In the example in FIG. 3*b*, an indication was received at 301*b* that a first individual was "Erin Mendel" and an indication was received at 302*b* that a second individual was "Ian Mendel." In the example in FIG. 3*b*, there is an indication at 301*b* that "Erin Mendel" is the daughter and an indication at 302*b* that "Ian Mendel" is the son. Thus, Erin Mendel and Ian Mendel are siblings. Again, however, an indication of the relationship between two individuals need not be received.

As in the example in FIG. 3*a*, at 305*b*, an indication of each of the 22 autosomal human chromosome pairs and the X and Y chromosomes is displayed. As shown at 305*b* and 304, the same symbol/color scheme is used to display the similarities in genotypic information as was used in FIG. 3*a*. As shown in FIG. 3*b* at 305*b*, an indication is displayed by the use of the color black, that Erin Mendel and Ian Mendel are identical at certain patches of their 22 autosomal human chromosome pairs and the X and Y chromosomes. Also, an indication is displayed by the use of the color blue, that Erin Mendel and Ian Mendel are half-identical at certain patches of their 22 autosomal human chromosome pairs and the X and Y chromosomes. Further, an indication is displayed by the use of the color white, that Erin Mendel and Ian Mendel are not identical at certain patches of their 22 autosomal human chromosome pairs and the X and Y chromosomes. There is also an indication displayed by the use of the color grey that there is not enough data at certain locations.

Figure 2B:
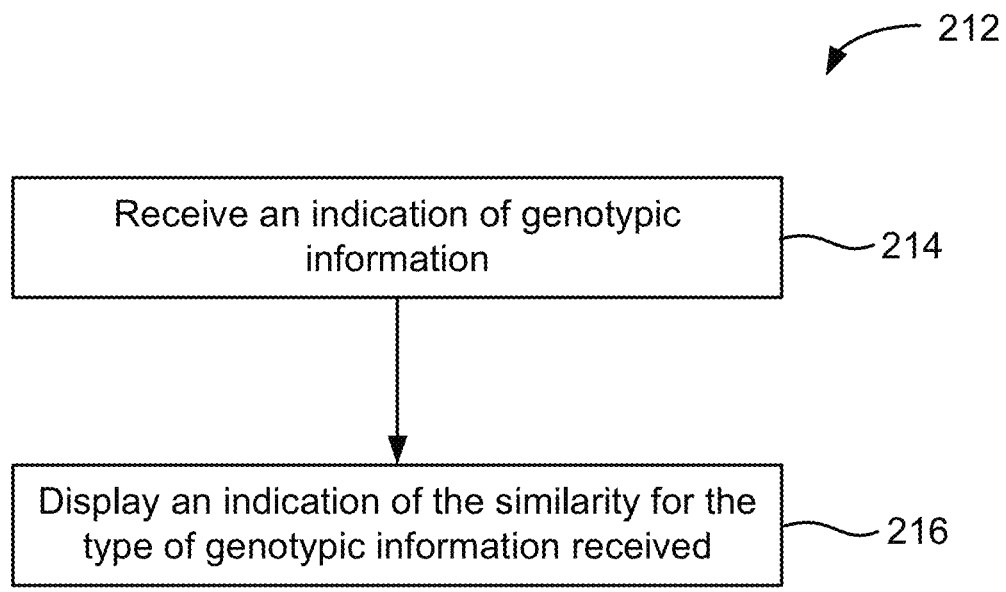
FIG. 2b is a flowchart illustrating an embodiment of a method for receiving an indication of a type of genotypic information and displaying an indication of the similarities between the at least two individuals for the type of genotypic information received.

FIG. 2b is a flowchart illustrating an embodiment of a method 212 for receiving an indication of a type of genotypic information and displaying an indication of the similarities between the at least two individuals for the type of genotypic information received. The steps in method 212 may be used in conjunction with the steps in method 200 illustrated in FIG. 2a. At step 214, an indication is received for a type of genotypic information for which an indication of the similarity should be displayed. This indication may include a comparison across all of the genome data, or a comparison of the genome data regarding a particular trait. Examples of particular traits may include: bitter tasting, circadian rhythm, endurance, female fertility, immune system compatibility, non-bitter tasting, pigmentation, weight body mass index, or other types of traits indicated by the user. In the example shown in FIG. 3a, the indication received is for a comparison across all of the genome data. As the example in FIG. 3a at 303 illustrates, a user interface may allow for receiving an indication of the type of genome data for the comparison by displaying on the screen a list of different genotypic data to compare and receiving an indication that a user has selected (e.g., by clicking) one of the items on the list. FIG. 3a, however is only one example of allowing for receiving such an indication. Other embodiments could include other ways for receiving an indication of the type of genome data for the comparison.

FIG. 3c is a screenshot illustrating another example of an interface displaying an indication of the similarity between two individuals' genotypic information. In the example shown in FIG. 3b, an indication was received at step 214 in FIG. 2b that an indication should be displayed for a comparison of the bitter tasting gene. As the example in FIG. 3c at 303c illustrates, a user interface may allow for receiving an indication of the type of genome data for the comparison by displaying on the screen a list of different genotypic data to compare and receiving an indication that a user has selected (e.g., by clicking) one of the items on the list. In the example illustrated in FIG. 3c, the user selected "bitter tasting." FIG. 3c, however only illustrates one example of allowing for receiving such an indication. Other embodiments could include other ways for receiving an indication of the type of genome data for the comparison.

In other embodiments, an indication may be received at step 214 that the genotypic information for which the comparison should be displayed is a user-specified type of genotypic information. For example, the user may type in a particular trait or location on the genome.

In the example in FIG. 3c, an indication was received at 301c that a first individual was "Erin Mendel" and an indication was received at 302c that a second individual was "Ian Mendel." In the example in FIG. 3c, there is an indication at 301c that "Erin Mendel" is the daughter and an indication at 302c that "Ian Mendel" is the son. Thus, Erin Mendel and Ian Mendel would be siblings. Again, however, an indication of the relationship between two individuals need not be received.

FIG. 3c illustrates an example of step 216 in FIG. 2a, i.e. an indication is displayed of the similarity of genotypic information between the at least two individuals for the indication of the type of genotypic information received in step 214. As in FIG. 3a, in the example illustrated in FIG. 3c at 305c, an indication of each of the 22 autosomal human chromosome pairs and the X and Y chromosomes is displayed. Again, as shown at 305c and 304, different colors are used to indicate the similarity between the genotypic information of at least two individuals. In the example shown in FIG. 3c at 304, blue is used to display an indication of which locations on the 22 autosomal human chromosome pairs and the X and Y chromosomes two individuals are half-identical. Black is used to display an indication of which locations on the 22 autosomal human chromosome pairs and the X and Y chromosomes two individuals are identical. White is used to indicate which regions have no DNA sequence in common and grey is used to indicate for which values there is not enough data to make a determination. Further, a red triangle is used to display an indication of the locations on the 22 autosomal human chromosome pairs and the X and Y chromosomes in which the genes associated with the particular trait appear. Because FIG. 3c displays an indication of all the location on the 22 autosomal human chromosome pairs and the X and Y chromosomes in which at least two individuals are identical, half-identical and not identical and also displays which locations are relevant to a particular trait, the example illustrates an indication of the similarities between the at least two individuals for that particular trait. An alternative embodiment could display only those particular genes relevant to a particular trait, as opposed to displaying all 22 autosomal human chromosome pairs and the X and Y chromosomes and other genes not associated with any particular trait as in FIG. 3c.

In a further example of a screen shot which displays an indication of the similarity between two individual's genotypic information, an indication may be received at step 214 that an indication should be displayed for a comparison across all of the genome data as discussed above. For example, an indication may be received that a first individual is "Greg Mendel" and an indication may be received that a second individual is a Chinese man.

In this example, as in FIGS. 3a-3b, at 304, blue is used to display an indication of which locations on the chromosome pairs two individuals are half-identical. Black is used to display an indication of which locations on the chromosome pairs two individuals are identical. White is used to indicate which regions have no DNA sequence in common and grey is used to indicate for which values there is not enough data to make a determination. Using these colors, an indication is displayed that Greg Mendel and the Chinese man are not identical at any locations in which there is enough data to make a determination.

Other embodiments could include other ways to display an indication of the similarities graphically.

In some embodiments the similarity may be shown for chromosome pairs separately so that one indicator, such as a graphical shape or a color, would be used to show identity across the paternal chromosome and another to show identity across the maternal chromosome.

Figure 5:
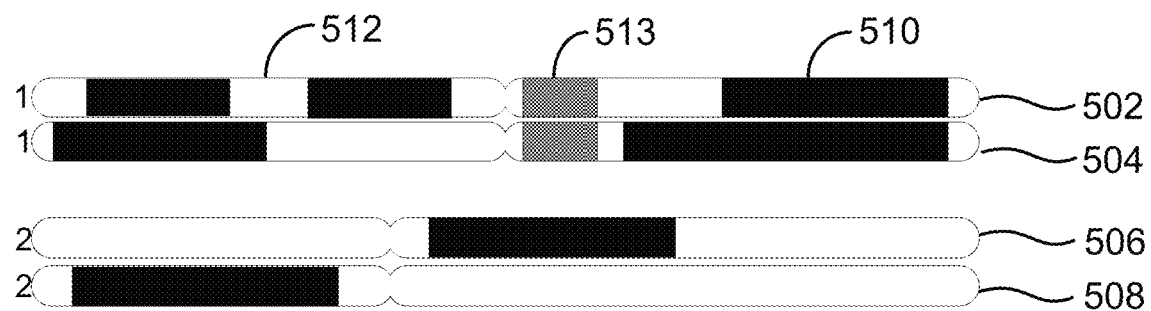
FIG. 5 is an example of a display illustrating an indication of the similarity between two individual's genotypic information using separate symbols to indicate each DNA sequence making up a chromosome pair when genotypic information is received in phased form.

In some embodiments the similarity may be shown using separate symbols to indicate each of the two DNA sequences making up a chromosome pair. FIG. 5 is an example of a display illustrating an indication of the similarity between two individual's genotypic information using separate symbols to indicate each DNA sequence making up a chromosome pair when genotypic information is received in phased form. In the example in FIG. 5, two separate bars, 502 and 504 are used to indicate each of the two DNA sequences for the first chromosome pair. Also, two separate bars, 506 and 508 are used to indicate the two DNA sequences making up the second chromosome pair. As illustrated on bar 502, at

510, a black symbol is used to indicate regions on one of the two DNA sequences for the first chromosome pair, which are the same for the individuals. At 512, a white symbol is used to indicate regions on one DNA sequences for the first chromosome pair in which the individuals are not similar. At 513, a grey symbol is used to indicate regions on the DNA sequence for which there is not enough genotypic information to make a comparison.

It is to be understood that FIG. 3*a-d* are only one example of displaying an indication of the similarity between two individuals. Alternative embodiments could include other ways to display an indication that the genotypic information of at least two individuals are half-identical at certain areas, are identical at certain other areas, and not identical at other areas. One example of an alternate embodiment would be to use as graphical symbols, rectangles of a first width or height to display an indication of areas that are half-identical, rectangles of a second width or height to indicate areas that are identical, and rectangles of a third width or height to display an indication that the areas are not identical. Other methods of displaying an indication of the similarity using symbols/colors could be used. For example, a display may include circles to represent areas that are half identical and squares to represent areas that are identical. In some embodiments, in place of shapes or colors, shading or other types of fill (e.g., hatching or cross-hatching) may be used.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A computer-implemented method comprising:
   receiving a selection of at least one of a first individual and a second individual;
   retrieving, from a database, representations of genetic sequences of the first individual and the second individual, wherein the genetic sequences include values for genetic markers therein;
   performing a window-based comparison of the representations of the genetic sequences of the first individual and the second individual;
   identifying, as identical segments, windows in which the values of the genetic markers in both of the genetic sequences are identical for the first individual and the second individual;
   identifying, as non-identical segments, the windows in which the values of the genetic markers are not identical for the first individual and the second individual; and
   providing for display, on a graphical user interface, a visual indication of the genetic sequences wherein: a first color, shading, or fill pattern is used to depict locations of the identical segments, and a second color, shading, or fill pattern is used to depict locations of the non-identical segments.

2. The computer-implemented method of claim 1, wherein the genetic sequences are diploid sequences, the method further comprising:
   identifying, as half-identical segments, the windows for which the values of the genetic markers in only one of the diploid sequences are identical for the first individual and the second individual, and
   wherein the visual indication of the genetic sequences includes a third color, shading, or fill pattern used to depict locations of the half-identical segments.

3. The computer-implemented method of claim 1, wherein the windows are of a fixed size.

4. The computer-implemented method of claim 3, wherein the fixed size is 10 Centimorgans in length.

5. The computer-implemented method of claim 1, wherein the visual indication includes a subset of the genetic sequences that are related to a type of the genetic sequences.

6. The computer-implemented method of claim 5, wherein the type comprises a particular trait or a particular location within the genetic sequences.

7. The computer-implemented method of claim 5, wherein the type is a one of traits relating to bitter tasting, circadian rhythm, endurance, female fertility, immune system compatibility, non-bitter tasting, pigmentation, or weight body mass index.

8. The computer-implemented method of claim 5, wherein the type comprises a user-specified type of genotypic information.

9. The computer-implemented method of claim 1, wherein the visual indication includes all of the genetic sequences for a given genome.

10. The computer-implemented method of claim 1, wherein a common shape is used to depict locations of the identical segments and the non-identical segments.

11. The computer-implemented method of claim 1, wherein different shapes are used to depict locations of the identical segments and the non-identical segments.

12. The computer-implemented method of claim 1, wherein a further color, shading, or fill pattern is used to depict segments that do not contain enough of the genetic markers to determine whether they are identical or non-identical.

13. The computer-implemented method of claim 1, wherein the visual indication of the genetic sequences for the identical segments and the non-identical segments include separate indications for each chromosome in the genetic sequences.

14. A non-transitory computer readable storage medium comprising computer instructions that, when executed by one or more processors, cause a computing system to perform operations comprising:
   receiving a selection of at least one of a first individual and a second individual;
   retrieving, from a database, representations of genetic sequences of the first individual and the second individual, wherein the genetic sequences include values for genetic markers therein;
   performing a window-based comparison of the representations of the genetic sequences of the first individual and the second individual;
   identifying, as identical segments, windows in which the values of the genetic markers in both of the genetic sequences are identical for the first individual and the second individual;
   identifying, as non-identical segments, the windows in which the values of the genetic markers are not identical for the first individual and the second individual; and
   providing for display, on a graphical user interface, a visual indication of the genetic sequences wherein: a first color, shading, or fill pattern is used to depict locations of the identical segments, and a second color, shading, or fill pattern is used to depict locations of the non-identical segments.

15. The non-transitory computer readable storage medium of claim 14, wherein the genetic sequences are diploid sequences, the operations further comprising:

identifying, as half-identical segments, the windows for which the values of the genetic markers in only one of the diploid sequences are identical for the first individual and the second individual, and wherein the visual indication of the genetic sequences includes a third color, shading, or fill pattern used to depict locations of the half-identical segments.

16. The non-transitory computer readable storage medium of claim 14, wherein the visual indication includes a subset of the genetic sequences that are related to a type of the genetic sequences, and wherein the type comprises a particular trait or a particular location within the genetic sequences.

17. The non-transitory computer readable storage medium of claim 14, wherein the visual indication includes a subset of the genetic sequences that are related to a type of the genetic sequences, and wherein the type is a one of traits relating to bitter tasting, circadian rhythm, endurance, female fertility, immune system compatibility, non-bitter tasting, pigmentation, or weight body mass index.

18. The non-transitory computer readable storage medium of claim 14, wherein a further color, shading, or fill pattern is used to depict segments that do not contain enough of the genetic markers to determine whether they are identical or non-identical.

19. The non-transitory computer readable storage medium of claim 14, wherein the visual indication of the genetic sequences for the identical segments and the non-identical segments include separate indications for each chromosome in the genetic sequences.

20. A computing system comprising:
one or more processors;
memory; and
program instructions, stored in the memory, that upon execution by the one or more processors cause the computing system to perform operations comprising:
receiving a selection of at least one of a first individual and a second individual;
retrieving, from a database, representations of genetic sequences of the first individual and the second individual, wherein the genetic sequences include values for genetic markers therein;
performing a window-based comparison of the representations of the genetic sequences of the first individual and the second individual;
identifying, as identical segments, windows in which the values of the genetic markers in both of the genetic sequences are identical for the first individual and the second individual;
identifying, as non-identical segments, the windows in which the values of the genetic markers are not identical for the first individual and the second individual; and
providing for display, on a graphical user interface, a visual indication of the genetic sequences wherein: a first color, shading, or fill pattern is used to depict locations of the identical segments, and a second color, shading, or fill pattern is used to depict locations of the non-identical segments.

* * * * *